(12) United States Patent
Johnson et al.

(10) Patent No.: US 6,526,306 B2
(45) Date of Patent: Feb. 25, 2003

(54) INTRAVAGINAL RADIOFREQUENCY IMAGING DEVICE

(75) Inventors: Vicki Young Johnson, Hoover, AL (US); Edward G. Walsh, Irondale, AL (US); Bradley R. Newcomer, Birmingham, AL (US); Mary Grace Umlauf, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 69 days.

(21) Appl. No.: 09/822,720

(22) Filed: Mar. 30, 2001

(65) Prior Publication Data

US 2001/0047132 A1 Nov. 29, 2001

Related U.S. Application Data

(60) Provisional application No. 60/193,229, filed on Mar. 30, 2000.

(51) Int. Cl.[7] .................................................. A61B 5/05
(52) U.S. Cl. ........................ 600/411; 600/410; 600/422; 600/423; 324/307; 324/309; 324/318
(58) Field of Search ................................. 324/300, 307, 324/304, 310, 312, 311, 315, 318, 322; 600/410, 423, 411, 422, 420, 421; 604/104, 97.02; 606/197, 195

(56) References Cited

U.S. PATENT DOCUMENTS

| 5,050,607 A | * | 9/1991 | Bradley et al. | .............. 600/423 |
| 5,355,087 A | | 10/1994 | Claiborne et al. | .......... 324/322 |
| 5,451,232 A | | 9/1995 | Rhinehart et al. | .......... 606/192 |

* cited by examiner

Primary Examiner—Marvin M. Lateef
Assistant Examiner—Jeoyuh Lin
(74) Attorney, Agent, or Firm—Benjamin Aaron Adler

(57) ABSTRACT

The present invention provides a vaginal imaging device for quantifying morphological and biochemical changes in the pelvic floor muscles as well as monitoring muscular function. Specifically, the present invention provides a vaginal imaging probe comprising a single or dual tuned resonator for both nuclear magnetic resonance imaging and spectroscopy of the pelvic floor musculature.

34 Claims, 6 Drawing Sheets

RF: Radiofrequency Tuning and Matching
F: Force Transducer
G: Gating Interface
MR: Magnetic Resonance Spectrometer

INTRAVAGINAL RADIOFREQUENCY IMAGING DEVICE

CROSS-REFERENCE TO RELATED APPLICATION

This non-provisional patent application claims benefit of provisional patent application U.S. Serial No. 60/193,229 filed Mar. 30, 2000, now abandoned.

BACKGROUND OF THE INVENTION

1. Field of the Invention

The present invention relates generally to the fields of medical devices and medical diagnostics and treatment. More specifically, the present invention relates to an intravaginal radiofrequency imaging device for intravaginal monitoring to assess the function, morphology, and exercise-induced metabolic and biochemical changes in the pelvic floor muscles surrounding the vaginal vault.

2. Description of the Related Art

Magnetic resonance imaging can be used for imaging of physiologic function, in addition to anatomical imaging. One such area is in the imaging of muscular function, both cardiac and skeletal muscle. A method for quantifying the contractile function of the heart is known as radiofrequency (RF) tagging. In this method, image data readout is preceded by a composite radiofrequency excitation that produces a series of dark parallel lines in the image. These lines result from the selective saturation of tissue within the field of view (FOV). In cardiac imaging, this excitation would be delivered on the R-wave trigger (i.e. at end diastole). Since material points in the tissue have been saturated, the lines are seen during image playback to move with the tissue as the heart contracts. Two such excitations can be used on the R-wave trigger to produce a grid of lines. An important feature of this method is that such images can be analyzed using automated techniques to track the tag line motion, and thus produce maps of strain and shear, as well as strain and shear rates.

It is also possible to produce strain and shear maps illustrating the function of skeletal muscle when a triggering signal representing a reproducible stimulus can be produced. Contractile force or pressure is such a reproducible stimulus.

The pelvic floor muscles provide support for the bladder, bladder neck and urethra. Urinary leakage occurs due to hypermobility of the urethra subsequent to a laxity of these muscles which results in inadequate urethral compression during increases in intra-abdominal pressure such as with coughing, rising from a seated position, or exercising.

Exercise to recondition the muscles of the pelvic floor is not a new concept. Specificity of training is paramount to achieve optimal functioning of the muscle for its intended use (Astrand & Rodahl, 1986; Hortobaghi, et al., 1991). Muscles of the levator ani, collectively called the pelvic floor musculature (PFM), are a heterogeneous mixture of 70% Type I (slow twitch) and 30% Type II (fast twitch) fibers (Critchley, et al., 1980; Gilpin, et al., 1989; Parks, et al., 1977). Type II muscle fibers are further delineated into Type IIa and Type IIb fibers. Type IIa fibers have a preponderance of glycolytic enzymes in their mitochondria, are larger in diameter and fatigue very quickly. In contrast, Type IIb fibers have fewer glycolytic enzymes in their mitochondria, are smaller in diameter, and are more resistant to fatigue.

Kegel (1948) introduced pelvic floor musculature exercises four decades ago with reported 69–93% success rates in treating females with stress urinary incontinence (SUI) (Jones & Kegel, 1952; Kegel, 1951; Kegel, 1956; Kegel & Powell, 1950). Studies that have examined muscle response to training have targeted Type II muscle fibers in strength-training regimens to recondition the pelvic floor musculature (Bo, et al., 1990; Burns, et al., 1993; Dougherty et al., 1993). However, these investigators merely hypothesized the mechanism for improvement as being exercise-induced hypertrophy because studies to describe the pelvic floor musculature in regard to muscle fiber type and mechanism of action have been limited to in vivo biopsy at the time of surgery or cadaver dissection (Gilpin et al., 1989).

Although there have been many advancements in the treatment of urinary incontinence using pelvic floor muscle exercises within a behavioral framework, investigators have been unable to describe the precise mechanisms of improvement. There are many potential and competing theories for the mechanisms of action responsible for recovery of continence. Some have hypothesized that increasing muscle strength allows the patient better sphincter control, while others have suggested that with exercise, the muscle size increases to provide additional occlusive bulk around the urethral sphincter.

There is little agreement on the correct technique for performing pelvic floor muscle exercise (Wells, 1990), and few studies to determine contraction intensity level of exercise to ensure success in pelvic floor musculature exercise therapy (Dougherty et al., 1993). Furthermore, no in vivo studies have shown the dynamic biochemical and metabolic changes that occur during or as a result of pelvic floor musculature exercise.

Most exercise protocols to improve function of the pelvic floor musculature have targeted strength enhancement and have been successful in decreasing leakage episodes. Descriptions of specific muscular responses resulting in functional changes of the pelvic floor musculature are inconsistent between studies. Factors attributed to functional changes include increased vaginal pressures, lengthening of the functional area of the urethra, and initial neural adaptation. One study used graded pelvic muscle exercises to strengthen the pelvic floor musculature and enhance endurance of muscle contractions in 65 women aged 35–75 years (Dougherty et al., 1993). This 16-week exercise protocol required exercises three times per week with measurements taken every 4 weeks. Gradation of the exercises involved maximal contraction effort that increased in number of contractions over the protocol period. Endurance exercises were maximum effort with emphasis on sustaining the contraction for 10 seconds. The investigators hypothesized that sustained pressure would benefit the Type I muscle fibers, while the repeated maximum contraction effort would benefit the Type II muscle fibers. Decreases in grams of urine loss were statistically significant (t=−4.7, p<0.0001). Episodes of leakage in 24 hours decreased from 2.6 to 1.0. There was no statistically significant correlation between urine loss and maximum pressure or between urine loss and sustained pressure. The investigators suggested that this finding might indicate that the mechanisms of pelvic floor musculature exercise affecting SUI are not explained by pressure changes alone. In fact, findings in a recent study (N=32) indicated that submaximal exercise not only increased endurance and resulted in decreases in quantity of urine leakage, but also was significantly more effective (t=1.75; p=0.045) for increases in strength of contraction effort than using a near-maximal exercise protocol (Johnson, 2001).

Technology is needed to enable investigators to describe the mechanisms responsible for improvement in continence.

The ability to analyze the regional mechanical and metabolic changes that occur in the pelvic floor musculature as a result of exercise might facilitate determining which exercise protocols are more effective and at what intensity the greatest improvement occurs. Strain and shear maps can reveal the presence of asymmetric function, or a subtle muscle injury such as internal perineal tear from birth injury. Investigation of the phosphorus metabolites and the pH would provide a chemical "snap-shot" of the cellular metabolism which can reveal abnormalities such as reduced perfusion. However, current technology requires tissue biopsy to conduct this type of analysis. Nuclear MRI and spectroscopy using state-of-the-art techniques to describe changes in the pelvic floor musculature structurally during exercise and conduct biochemical and metabolic analyses as subjects exercise and improve over time, might give researchers insight into the mechanisms responsible for change and improvement without the need for invasive biopsy.

MRI has been used to visualize pelvic floor musculature contractions in normal females (N=6). Findings showed that pelvic floor musculature contractions using MRI could be identified and that anatomical displacement of the bladder could be demonstrated. This study used coronal and sagittal planes for imaging (Christensen et al., 1995). However, no study has reported use of an insertable vaginal device with incorporation of force transduction and phosphorus spectroscopy to allow investigators the ability to conduct force of contraction measurements and biochemical analyses without the need for tissue biopsy.

The prior art is deficient in the lack of a non-invasive device/means of intravaginal monitoring. Specifically, the prior art is deficient in the lack of an intravaginal imaging device for monitoring and conducting biochemical analysis, wherein the imaging device combines a NMR resonator and force transduction mechanism in a single device. The present invention fulfills this long-standing need and desire in the art.

SUMMARY OF THE INVENTION

The present invention provides a vaginal imaging probe (VIP), an intravaginal probe for quantifying morphological and biochemical changes in the pelvic floor muscles as well as monitoring muscular function. This vaginal imaging probe acts as a dual frequency (proton, $^{31}$phosphorus) transmit/receive antenna for magnetic resonance (MR) imaging and spectroscopy of the musculature which contributes to urinary continence. Additionally, the vaginal imaging probe incorporates a force transducer to measure the force of muscular contractions, and to permit triggering of image acquisitions according to the developed force levels.

In one embodiment of the present invention, there is provided a vaginal imaging device, comprising a single or dual tuned resonator and a force transduction mechanism to permit triggering of a scanner to produce vaginal nuclear magnetic resonance imaging and spectroscopy data. In one aspect, the resonator comprises a transmit/receive element which is a single turn solenoid oriented to permit non-gradient localized spectroscopy. Moreover, a vial containing a 300 mM inorganic phosphate reference solution is located at the center of the loop of the single turn solenoid to allow chemical shift referencing for the signals obtained. In another aspect, the transmit/receive element of the resonator is an array of individual antenna elements located around the long axis of the device for the purpose of providing a different spatial sensitivity profile than that provided by a single turn solenoid. The means to trigger the resonator can be provided by a piezoelectric force transducer, a resistive force transducer or a pneumatic pressure transducer. Such a vaginal imaging device is useful for radiofrequency tagged magnetic resonance imaging, phase velocity mapping, diffusion weighted imaging as well as non-gradient localized phosphorus spectroscopy.

In another embodiment of the present invention, there is provided a vaginal imaging device, comprising a single or dual tuned imaging and spectroscopy resonator and a force transducer encased in a magnetic resonance imaging compatible housing; a compliant and hollow disposable housing that allows pneumatic transduction of contraction effort; and a means to transmit the air pressure in the disposable housing to the force transducer. The resonator comprises a transmit/receive element which may be a single turn solenoid with a vial containing a 300 mM inorganic phosphate reference solution located at the center of the loop of the single turn solenoid to allow chemical shift referencing for the signals obtained. The force transducer can be a piezoelectric force transducer, resistive force transducer or pneumatic pressure transducer. Such a vaginal imaging device produces radiofrequency tagged magnetic resonance imaging and non-gradient localized phosphorus spectroscopy.

In other embodiments of the present invention, there are provided methods of imaging and assessing biochemical states in pelvic floor musculature in situations such as before and after exercise, before and after surgical repair and before and after pharmaceutical therapy in individual suffering from abnormalities in pelvic floor musculature.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
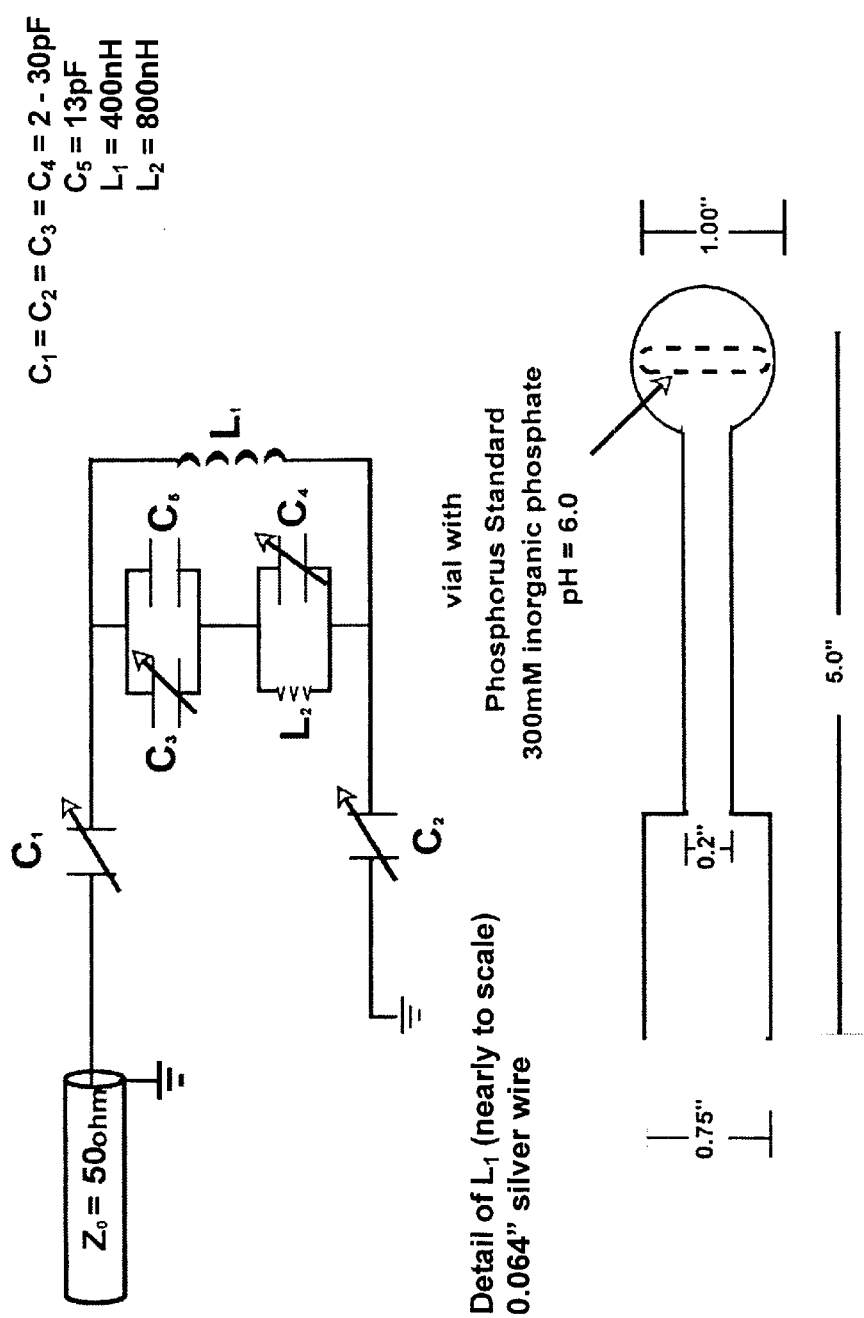
FIG. 1 shows a radiofrequency tuning/matching circuit with detail of antenna element showing phosphorus reference.

The present invention provides a vaginal imaging probe for internal and/or intravaginal monitoring of pressure during contractions, magnetic resonance imaging (MRI), spectroscopy, and tagging of the levator ani musculature. The device of the present invention allows analysis of biochemical changes, muscle density and morphology, and regional muscle function and strength in response to exercise of the pelvic floor musculature. More specifically, monitored biochemical changes include oxidative capacity, capillary bed blood flow, and mitochondrial content. Potential applications include, but are not limited to, description of the architectural morphology of the levator ani musculature, quantification of exercise-induced changes in the pelvic floor muscles such as muscle density, asymmetry during contractions and biochemical changes.

The presently disclosed vaginal imaging device includes variable capacitors with adjustment mechanisms and a dual tuned radiofrequency imaging/phosphorus spectroscopy coil. The permanent housing of the device contains the radiofrequency tuning/matching circuit, and a pneumatic force transducer in one preferred embodiment. The disposable portion (inserted into the vagina) contains the antenna element and phosphorus standard, and is made of a compliant material that can deform when the subject produces a contraction effort, thus changing its volume, and therefore internal air pressure. This pressure is coupled to the pneumatic transducer by an airtight connection to the permanent housing. The disposable housing can also be pre-pressurized to add mechanical stability once inserted using a syringe attached to a luer-lock fitting at the back of the permanent housing.

The vaginal imaging probe is designed for conducting intravaginal, non-invasive magnetic resonance imaging to measure strength, architectural morphology, and biochemical analysis while providing a mechanism for force activated triggering of the MR scanner. Application of this device differs from current MRI techniques for examining the levator muscles by allowing 360 degrees of internal, intravaginal imaging, and the ability to conduct biochemical analysis of the tissue (i.e., spectroscopy) along with muscle biomechanics information through high resolution RF tagged imaging techniques.

The vaginal imaging probe provides capabilities that exceed those available currently in urodynamic technology or standard magnetic resonance imaging (MRI). This proposed device offers clinical investigators the instrumentation to examine several mechanisms of urinary control that have been beyond the state-of-the-science in continence research and diagnostics. Clinicians are able to individually quantitate the structural, metabolic, and biochemical dysfunction of each patient, which has direct implications for the selection and development of the most cost-effective and appropriate treatment on a case-by-case basis.

Investigation of the phosphorus metabolites and the pH provides a non-invasive, chemical "snap-shot" of the cellular metabolism. Owing to the non-invasive and painless technique, the need for muscle biopsy to describe the effects of exercise in biobehavior treatment of urinary incontinence and determination of the mechanism of action for these non-surgical therapies is eliminated. Previously, studies involving the circumvaginal musculature in regard to muscle fiber type and mechanism of action have been limited to in vivo biopsy or cadaver dissection. Imaging and spectroscopy using the vaginal imaging probe disclosed herein will also enable pre- and post-comparison of various techniques of surgical repair for bladder prolapse, cystocele repair, and pelvic sling procedures. Whereas surgical treatment is sometimes warranted, the efficacy of specific procedures remain in debate. This addition to the body of knowledge in treatment of urinary incontinence may provide quantifiable evidence of the efficacy for non-surgical treatments for incontinence, justification for medical coverage, and reimbursement to third party for these therapies. The non-invasive nature of this technology lends itself to time-resolved investigations and repeat studies. Although muscle biopsies may provide similar information, these biopsies are often painful to subjects, are not conducive to studies that require repeated measures, and may result in additional destruction of tissue and nerves in an already compromised musculature. The present vaginal imaging probe is designed to solve the above problems.

Rectal use for diagnosis of fecal incontinence is possible with an embodiment of this device in which the diameter of the disposable housing is reduced to 1.25–1.75 cm.

In the present invention, the following terms shall be interpreted according to the definitions set forth below. Terms not defined infra shall be interpreted according to the ordinary and standard usage in the art.

As used herein, "pelvic floor musculature (PFM)" shall refer to the levator ani muscles, specifically the coccygeous, pubococcygeous, and iliococcygeous through which the sphincter vaginae and compressor urethrae pass.

As used herein, "piezoelectric force transducer" shall refer to the device which converts applied force into a force-proportional electrical signal.

As used herein, "resistive force transducer" shall refer to a device in which resistance varies with applied force, either through incorporation of a force dependent resistance in a bridge circuit (Wheatstone bridge) or through use of a material whose intrinsic resistance varies with pressure.

As used herein, "pneumatic pressure transducer" shall refer to a device that converts air pressure into a pressure proportional voltage.

As used herein, "contractile force perpendicular" shall refer to force applied perpendicular to the long axis of the vaginal imaging probe.

As used herein, "single-turn solenoid" shall refer to the radiating and receiving element of the vaginal imaging probe.

As used herein, "non-gradient, localized spectroscopy" shall refer to spectroscopy in which data is acquired from the entire sensitive volume of the vaginal imaging probe.

As used herein, "radiofrequency (RF) tagged image" shall refer to images in which a grid of dark tag lines are produced in a series of images to permit assessment of regional tissue motion.

As used herein, "phase velocity mapping" shall refer to an MR imaging technique in which motion sensitizing gradient pulses are used to produce images in which pixel intensities correspond to velocity of blood or tissue during the imaging acquisition.

As used herein, "diffusion weighted imaging" shall refer to an MR imaging technique in which gradient pulses are used to sensitize an image acquisition to random diffusion. This method permits assessment of diffusion components in specific directions.

As used herein, "force-based trigging" shall refer to acquisition of image data at pre-set force levels.

As used herein, "gating mechanism" shall refer to the device which reads the force transducer signal and produces trigger pulses for the scanner at pre-set force levels.

As used herein, "field strength" shall refer to the main magnetic field strength of the scanner.

In one embodiment of the present invention, there is provided a vaginal imaging device, comprising a single or dual tuned resonator and a force transduction mechanism to trigger the resonator to produce vaginal nuclear magnetic resonance imaging and spectroscopy data. In one aspect, the resonator comprises transmit/receive element which is a single turn solenoid oriented to permit non-gradient localized spectroscopy. Moreover, a vial containing a 300 mM inorganic phosphate reference solution is located at the center of the loop of the single turn solenoid to allow chemical shift referencing for the signals obtained. In another aspect, the transmit/receive element of the resonator is an array of individual antenna elements located around the long axis of the device for the purpose of providing a different spatial sensitivity profile than that provided by a single turn solenoid. The means to trigger the resonator can be provided by a piezoelectric force transducer, a resistive force transducer or a pneumatic pressure transducer. Such a vaginal imaging device is useful for radiofrequency tagged magnetic resonance imaging, phase velocity mapping, diffusion weighted imaging as well as non-gradient localized phosphorus spectroscopy.

In another embodiment of the present invention, there is provided a vaginal imaging device, comprising a single or dual tuned imaging and spectroscopy resonator and a force transducer encased in a magnetic resonance imaging compatible housing; a compliant and hollow disposable housing that allows pneumatic transduction of contraction effort; and a mean to transmit the air pressure in the disposable housing to the force transducer. The resonator comprises transmit/receive element which is a single turn solenoid with a vial containing a 300 mM inorganic phosphate reference solution located at the center of the loop of the single turn solenoid to allow chemical shift referencing for the signals obtained. The force transducer can be, for example, a piezoelectric force transducer, resistive force transducer or pneumatic pressure transducer. This vaginal imaging device produces radiofrequency tagged magnetic resonance imaging and non-gradient localized phosphorus spectroscopy.

In still another embodiment of the present invention, there is provided a method for imaging pelvic floor musculature in a subject, comprising the step of applying the vaginal imaging device disclosed herein to the subject, thereby produce an image of the pelvic floor musculature.

In another embodiment of the present invention, there is provided a method of obtaining spectroscopic information on the biochemical state of the pelvic floor musculature by applying the vaginal imaging device disclosed herein to a subject to produce magnetic resonance spectroscopic information that provides an assessment of muscular biochemical activity.

In yet another embodiment of the present invention, there is provided a method of assessing biochemical changes under exercise conditions in pelvic floor musculature by applying the vaginal imaging device disclosed herein to a subject to acquire magnetic resonance spectroscopic data before, during and after the exercise conditions.

In yet another embodiment of the present invention, there is provided a method of evaluating efficacy of a surgical repair in pelvic floor musculature in an individual by applying the vaginal imaging device disclosed herein to such individual before and after the surgical repair.

In still yet another embodiment of the present invention, there is provided a method for evaluating efficacy of an exercise therapy in an individual by applying the vaginal imaging device disclosed herein to such individual before and after the exercise therapy.

In still yet another embodiment of the present invention, there is provided a method for evaluating efficacy of a pharmaceutical therapy in an individual suffering from abnormalities in pelvic floor musculature by applying the vaginal imaging device disclosed herein to such individual before and after the pharmaceutical therapy.

The following examples are given for the purpose of illustrating various embodiments of the invention and are not meant to limit the present invention in any fashion.

EXAMPLE 1

Vaginal Imaging Probe Design

The vaginal imaging device (VIP) disclosed herein incorporates prior art design in terms of structural housing for the device. The initial vaginal pressure probe was described by Dr. Arnold Kegel in 1948 in the development of a perineometer for measuring pressure changes in response to pelvic floor muscle contraction. Although improvements in the perineometer have resulted in various shapes, sizes, and material composition, the overall concept of an insertable vaginal probe has been shown to be safe and efficacious. The vaginal imaging probe of the present invention improves upon the previous designs' structure to facilitate functional placement for maximal visualization and measurement of force conduction, and placement of a coil within the probe for imaging and spectroscopy.

Figure 5:
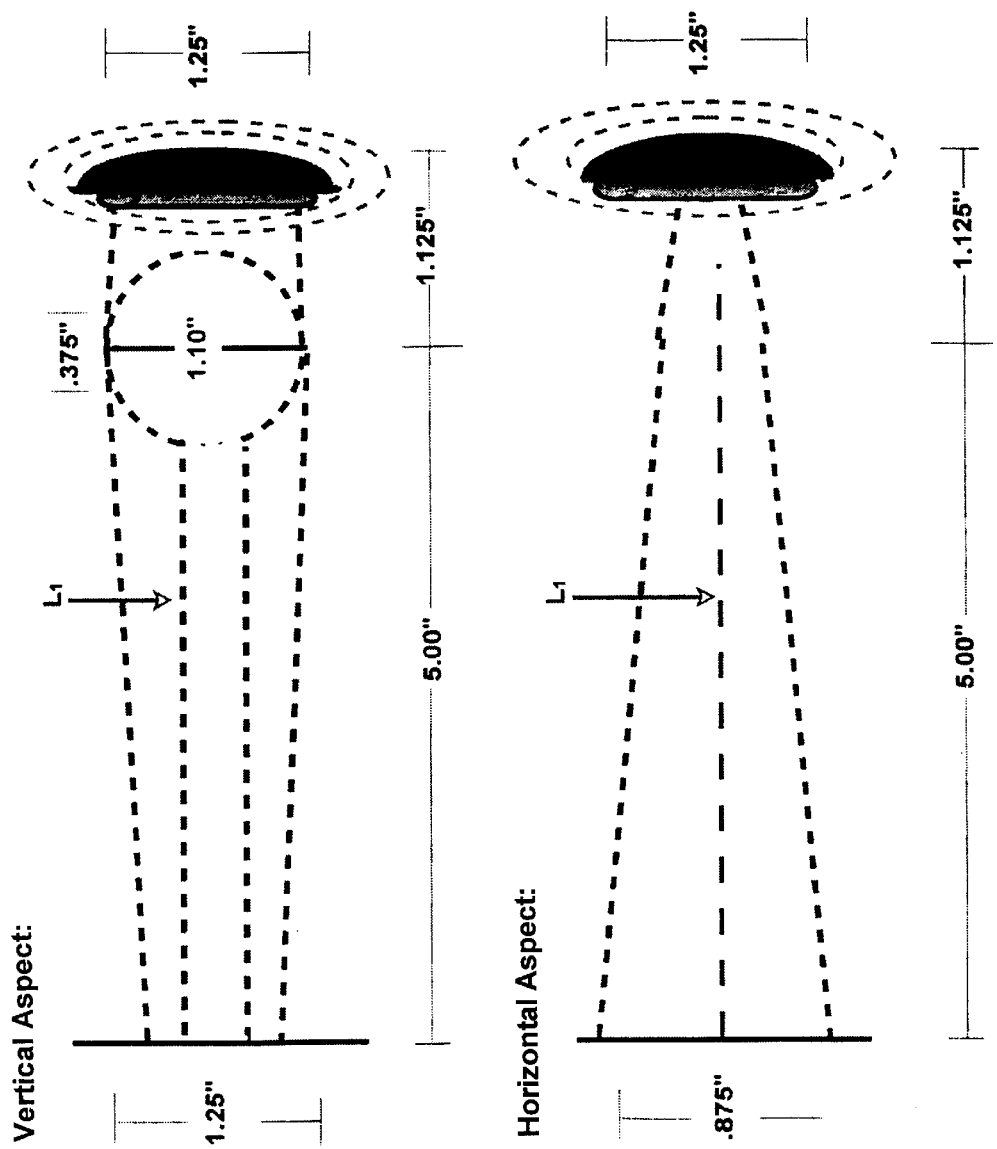
FIG. 5 shows the layout and geometry of the disposable portion of the resonator.

The vaginal imaging probe (VIP) is a single or dual-tuned resonator for nuclear magnetic resonance (NMR) imaging and spectroscopy. The vaginal imaging probe also has the ability to measure contractile force perpendicular to its long axis. This is accomplished using preferably a pneumatic force transduction mechanism producing a direct current (DC) signal proportional to developed force. The probe consists of two portions, a permanent unit enclosing the RF tuning/matching circuit (FIGS. 1 and 2) and pressure transducer, along with interconnections for same, and a disposable component containing the antenna element. The disposable component has a compliant, hollow housing (FIG. 5). Contraction force exerted by the subject results in a change in the volume of the compliant housing, increasing its internal air pressure. This change in pressure is detected by the force transducer and reflected in its output signal. Pressure measurements can be made continuously during the course of a study. The disposable housing also incorporates an annular inflatable ring at its end which expands under pressurization to provide for mechanical stabilization.

Figure 2:
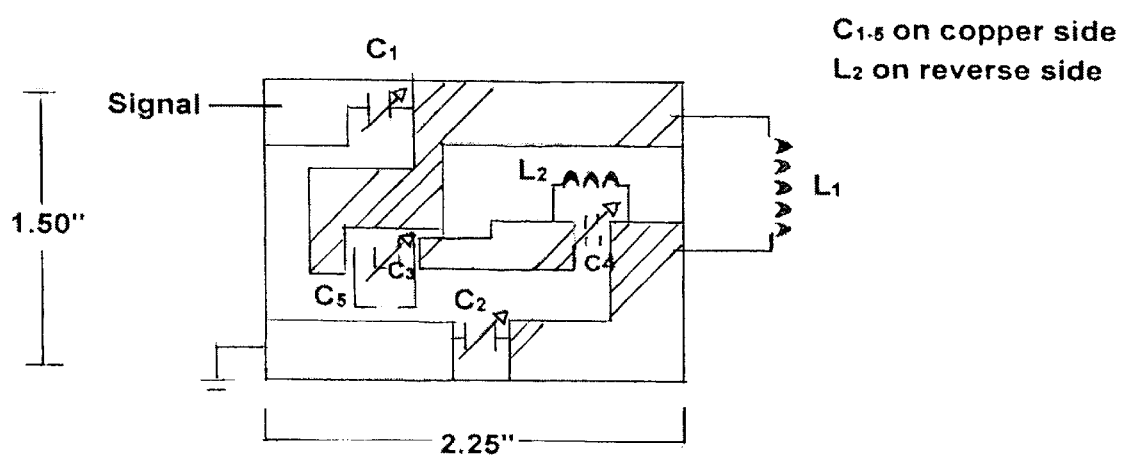
FIG. 2 shows a printed circuit board layout of tuning/matching circuit.

The tuning/matching circuit is intended to produce a 50Ω input impedance at two different resonant frequencies, corresponding to the $^1$H and (typically) $^{31}$P resonant frequencies (FIG. 1). The second nucleus can also be selected to be $^{23}$Na, $^{13}$C, etc. for purposes of spectroscopic studies. The two variable capacitors in series with the two coaxial cable conductors ($C_1$ and $C_2$) are primarily responsible for establishing the input impedance, whereas the remaining capacitors ($C_3$ and $C_4$) are primarily responsible for establishing the frequencies of the resonances (defined as the frequencies where an input impedance of 50Ω is achieved). The circuit is mounted on a printed circuit board as shown in FIG. 2. In another embodiment of this device, the tuning/matching circuit is single tuned (typically to $^1$H for imaging purposes). In this embodiment, the parallel capacitor/inductor combination ($L_2$–$C_4$) is deleted.

Figure 3:
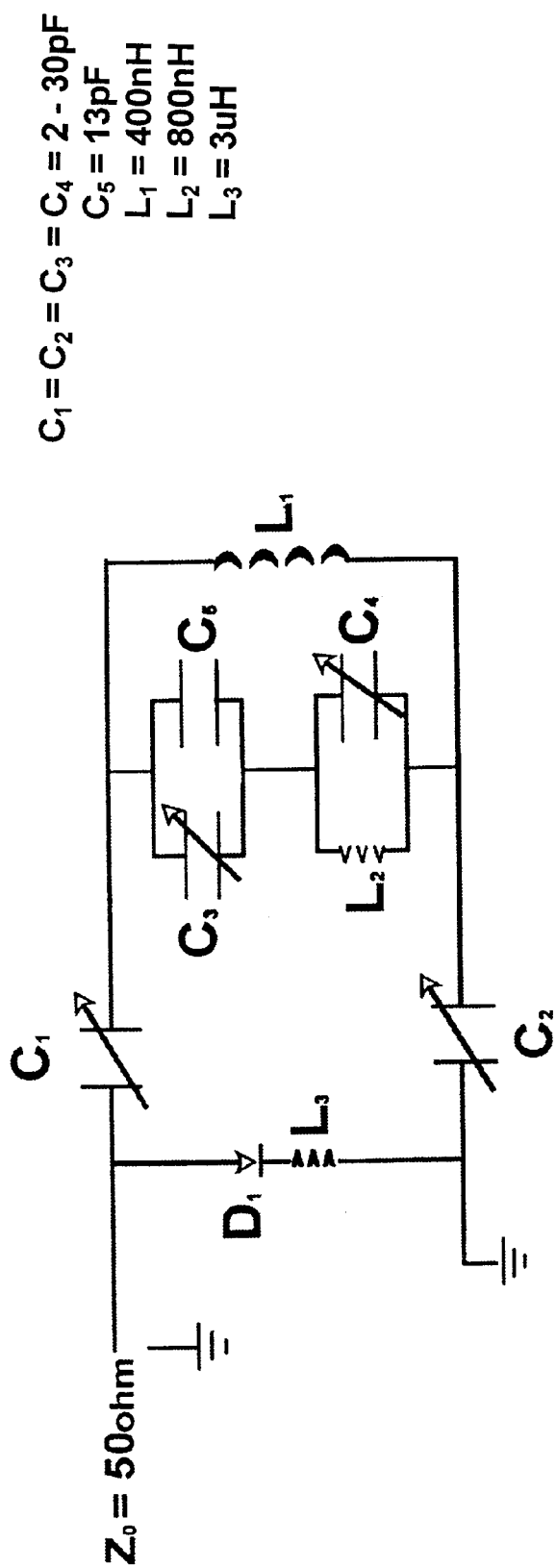
FIG. 3 shows the radiofrequency tuning/matching circuit incorporating active decoupling for use as a receive only resonator.

In an embodiment permitting use of the probe as a receive-only resonator, active and passive decoupling circuits can be included as shown in FIG. 3. In the active mode, the PIN diode is brought into conduction by a bias signal sent by the scanner. This causes bypass of $C_3$ shifting the resonant frequency upward, and making the probe non-responsive at the imaging frequency, thereby preventing local retransmit of the RF excitation originating from the scanner's volume resonator. As a redundancy mechanism, a passive decoupling circuit consisting of a pair of crossed PIN diodes across $L_1$. This mechanism does not require a bias signal from the scanner. When the volume resonator transmits, the diodes go into conduction and bypass $L_1$ resulting in a change in the resonant frequency, making the probe non-responsive at the imaging frequency and preventing local retransmit of the RF excitation originating from the scanner's volume resonator (again, to prevent undesired tissue heating).

Figure 4:
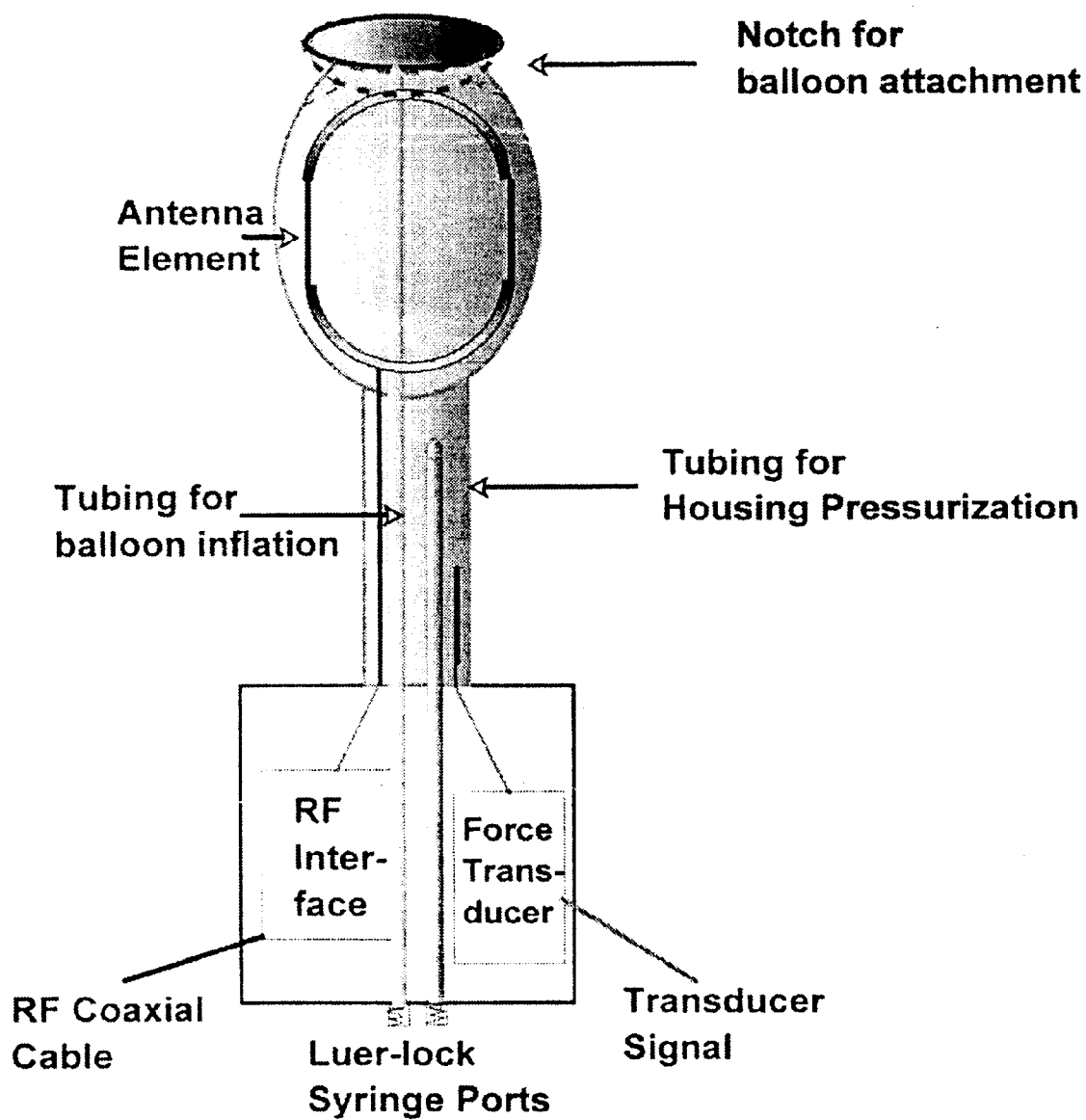
FIG. 4 shows the layout of components for the housings of the probe.

Also contained in the non-disposable housing is a pneumatic pressure transducer for contraction force measurement. A representative device is the Motorola MPX10 series of silicon film pressure transducers. A small tube within the housing connects the pressure port of the transducer to a port on the housing where communication is made with the volume enclosed by the disposable housing containing the antenna element as shown in FIG. 4. Provision is made for delivery of a DC bias signal to the transducer (for the Motorola MPX series, a 5V bias can be used), and for obtaining the force proportional output signal for delivery to a gating unit to synchronize the MRI scanner.

The attachment of the disposable portion of the probe to the main housing is made through an airtight fitting to permit the internal volume of the disposable housing to function as a changeable volume for pressure transduction. Also contained in the main housing is a tube allowing connection of a syringe to add air pressure to the disposable housing to provide for mechanical stabilization once inserted.

The antenna element consists of a single turn solenoid as shown in FIG. 1. Mounted at the center of the loop is a small glass vial containing a 300 mM solution of inorganic phosphate at pH 7.4. This solution acts as a chemical shift reference for phosphorus spectroscopy to permit positive identification of the ATP and PCr peaks in the muscle spectra, and to provide a reference for deriving tissue pH from the chemical shift difference between PCr and inorganic phosphate (which has a pH dependence). In another embodiment, the antenna element consists of multiple loops established as a phased array, to alter the sensitivity profile of the device for more uniform coverage around the long axis of the probe.

The vaginal imaging probe, by virtue of its ability to produce a confined radiofrequency (RF) magnetic field, permits imaging of the levator ani muscles with a greater spatial resolution than is possible using conventional volume resonators. When the field-of-view on a MR scanner is set to be smaller than the object being imaged, signal from outside the defined region can "fold over" into the image field. In effect, when the field-of-view is set to be smaller than the object, the signals received are effectively under-sampled which manifests itself as "fold over". The vaginal imaging probe, however, confines the radiofrequency excitation to a region within 2 centimeters of itself, permitting the field-of-view to be set to as little as 4 centimeters, without concern for fold over, since tissue beyond this region is not being excited to produce any signal. Spatial resolution improvement on the order of a factor of 6–10 over volume resonator imaging is therefore possible. The restricted transmit field allows setting of the field-of-view of the NMR scanner to its minimum value, thus maximizing spatial resolution without concern for fold-over artifact which can occur when NMR signals originate outside of the selected field-of-view. The element is designed to transmit and receive and is oriented to accomplish imaging and spectroscopy of the levator ani musculature through which the sphincter vaginae and compressor urethrae pass.

The design of the vaginal imaging probe allows non-gradient, localized phosphorus-31 spectroscopy of the levator ani muscles for assessment of metabolic function. The benefit of non-localized spectroscopy includes improved signal-to-noise ratio (SNR) and quantifiable improvement of temporal resolution over volume selective acquisitions. Spectroscopy of these muscles enables acquisition of $^{31}P$ MR spectra, which provides information in regard to intracellular levels of adenosine triphosphate (ATP), phosphocreatine (PCr), inorganic phosphate (Pi), phosphomonoesters, and phosphodiesters. Measurements of intracellular pH are also obtained from these $^{31}P$ MR spectra. The vaginal imaging probe includes an internal phosphorus reference to permit absolute quantification of phosphorus metabolites.

Figure 6:
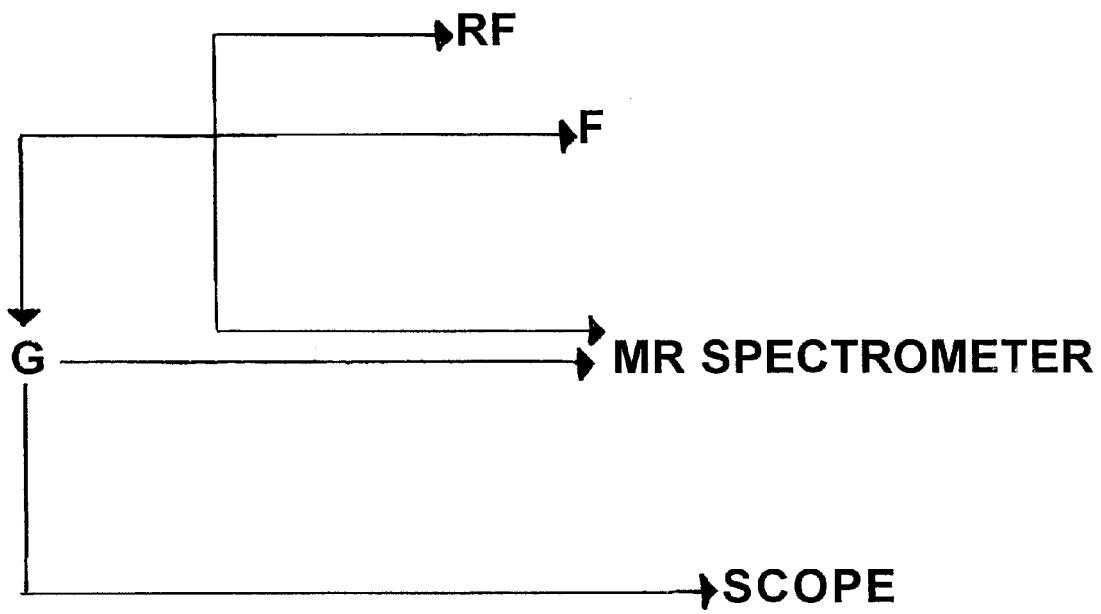
FIG. 6 shows the interconnections of components for use of the vaginal imaging probe.

The interconnections and relationships between the components of the probe and the MRI scanner are shown in FIG. 6. A gating interface is used to provide DC bias to the pressure transducer in the main housing, and to receive and process the force proportional signal delivered by the transducer. The gating interface (connected to the scanner) can be used to issue control signals to the scanner when the patient exerts specified levels of contraction effort. A 50Ω coaxial cable delivers the RF transmit excitation to the probe, and carries the received NMR signal to the scanner receiver. In another embodiment of the probe as a receive only device, the coaxial cable is used only to deliver the received NMR signal to the scanner receiver.

EXAMPLE 2

Components of the Vaginal Imaging Device and Operation Principle

The vaginal imaging probe (VIP) is the first to combine a resonator with a force measuring mechanism. A force gating mechanism is used in the urinary incontinence studies using vaginal imaging probe. The purpose of studies using the device is to collect and analyze quantitative information regarding the mechanical function of the pelvic floor muscles that are responsible for attaining and maintaining urinary continence. Radiofrequency tagged images are acquired at rest and at various contraction effort levels. The regional function of the muscles is reflected in the distortion of the tag lines. Thus, global depression of function, as well as regional abnormalities resulting from injury (childbirth or surgery) or neurological dysfunction can be distinguished. Such force-based triggering can also be applied to $^{31}P$ spectroscopy studies to examine the metabolic activity of the muscles during exercise at various levels of contraction effort. Use of the vaginal imaging probe for functional muscle imaging requires use of the force triggering mechanism.

The coaxial fed resonator consists of a dual resonant matching circuit which permits impedance matching of the resonator to the characteristic impedance of the radiofrequency transmission network of the NMR scanner (50 ohms). The transmit/receive element is a single turn solenoid oriented such that the sensitive region corresponds to the muscles of interest, permitting the non-gradient localized spectroscopy to be performed. This radiofrequency field profile also permits high resolution imaging to be performed through reduction of the field-of-view since the signal is inherently confined to the anatomy under consideration. Incorporated into the device is a pneumatic, piezoelectric or resistive force transducer for measurement of developed contractile force, both for monitoring of subject progress, and to provide a force proportional gating signal for the scanner (necessary for imaging of mechanical function in a reproducible fashion).

During operation, a radiofrequency signal fed to the vaginal imaging probe produces a corresponding radiofrequency magnetic field in the tissue of interest. The frequency of this field corresponds to the resonant frequency of the nuclei to be examined and produces a stimulated signal. This stimulated signal is received by the vaginal imaging probe which converts it to a corresponding electrical signal. This electrical signal is amplified and processed to produce image and spectroscopy data. Force transduction for measurement of muscular function is accomplished using a pneumatic, piezoelectric (charge proportional to force) or resistive bridge (voltage proportional to force) transducer.

The prototype device is designed for use at 4.1 Telsa (T) ($^1$H frequency=174.86 MHz, $^{31}$P frequency=70.8 MHz); however, the device can also be used at 1.5 T ($^1$H frequency= 63 MHz, $^{31}$P frequency=25.5. MHz). The most common main field strength in the base of installed clinical NMR scanners is 1.5 T. The primary sacrifice of the lower field strength is reduction of the signal to noise ratio for the phosphorus spectroscopy. However, the signal to noise ratio should remain adequate for diagnostic purposes as demonstrated in other applications, such as cardiac spectroscopy.

The prototype device was hand fabricated and assembled. The matching circuit and transmit/receive element were bench tested using a network analyzer to assess proper electrical function. Image and spectroscopy testing were carried out in phantoms to ensure proper localization of the radiofrequency magnetic field. Insulation properties were tested by raising input power to the dielectric breakdown limits of the capacitors in the matching circuit (80 watts input power, beyond the limits that would be applied in actual application). The vaginal imaging probe is tested for current leakage according to normal hospital clinical biomedical engineering practice.

Thus, in view of the detailed disclosure above, the present invention is directed to a vaginal imaging device, comprising: a single or dual tuned resonator comprising a transmit/receive element for nuclear magnetic resonance imaging and spectroscopy; and a force transduction mechanism for monitoring a subject's contraction effort and to permit triggering of a scanner to produce vaginal imaging and spectroscopy data. The single tuned resonator may be used for nuclear magnetic resonance imaging using the $^1$H isotope. The tuned resonator may be used for $^1$H isotope imaging and for performing nuclear magnetic resonance spectroscopy of a second isotope selected from the group consisting of $^-$P, $^{13}$C, $^{23}$Na, $^{39}$K and $^{43}$Ca. Generally, the transmit/receive element is a single turn solenoid oriented to permit non-gradient localized spectroscopy. In one aspect, a vial containing a 300 mM inorganic phosphate reference solution is located at the center of the loop of said single turn solenoid to allow chemical shift referencing for the signals obtained. Generally, the transmit/receive element is an array of individual antenna elements located around the long axis of the device for the purpose of providing a different spatial sensitivity profile than that provided by a single turn solenoid. The force transduction mechanism is used to monitor contraction effort of the subject for the purpose of synchronizing scanner image or spectroscopy data acquisition with the contraction effort of the subject. The force transduction mechanism may be used to synchronize scanner image acqusition with the scanner body volume resonator acting as the transmit/and or receive antenna. The force transduction mechanism may be used to synchronize scanner image or spectroscopy data acquisition with its own antenna element in a transmit/receive mode. In another aspect, the force transduction mechanism is used to synchronize scanner image or spectroscopy data acquisition with its own antenna element in a receive only mode with active or passive decoupling, wherein said decoupling prevents local retransmit of the radiofrequency signal and excessive tissue heating. Preferably, the force transduction mechanism is selected from the group consisting of piezoelectric force transducer, resistive force transducer and pneumatic pressure transducer. Representative imaging techniques useful in this methodology include radiofrequency tagged magnetic resonance imaging, phase velocity mapping and diffusion weighted imaging. In this method, the spectroscopy may be non-gradient localized phosphorus spectroscopy.

The present invention is also directed to a vaginal imaging device, comprising: (a) a single or dual tuned imaging and spectroscopy resonator and matching network; (b) a force transducer that produces a force proportional gating signal to trigger a scanner to produce vaginal imaging and spectroscopy data at user-defined force levels; (c) a magnetic resonance imaging compatible housing encasing (a) and (b); (d) a compliant and hollow disposable housing that allows pneumatic transduction of contraction effort, wherein said disposable housing contains the antenna element of said resonator; and (e) a mean to transmit the air pressure in said disposable housing to said force transducer located in the permanent housing. The disposable housing may contain a locator ring to ensure correct positioning of said device. An an inflatable annular cuff that can be independently pressurized to provide for mechanical stabilization is located on the outside of said disposable housing near the tip. Generally, the force transducer is a piezoelectric force transducer, a resistive force transducer or a pneumatic pressure transducer. In one aspect, the antenna element of said resonator is a single turn solenoid oriented to permit non-gradient localized spectroscopy. A vial containing a 300 mM inorganic phosphate reference solution may be located at the center of the loop of said single turn solenoid to allow chemical shift referencing for the signals obtained. The imaging technique may be radiofrequency tagged magnetic resonance imaging and the spectroscopy may be non-gradient localized phosphorus spectroscopy.

The present invention is also directed to a method for imaging pelvic floor musculature in a subject, comprising the step of: applying the vaginal imaging device of described above to a subject to produce an image of the pelvic floor musculature.

The present invention is also directed to a method for imaging pelvic floor musculature in a subject, comprising the step of: applying the vaginal imaging device described above to a subject to produce an image of the pelvic floor musculature.

The present invention is also directed to a method for obtaining spectroscopic information on the biochemical state of pelvic floor musculature in a subject, comprising the step of: applying the vaginal imaging device described above to a subject to produce magnetic resonance spectroscopic information which provides assessment of muscular biochemical activity.

The present invention is also directed to a method for obtaining spectroscopic information on the biochemical state of pelvic floor musculature in a subject, comprising the step of: applying the vaginal imaging device described above to a subject to produce magnetic resonance spectroscopic information which provides assessment of muscular biochemical activity.

The present invention is also directed to a method for assessing biochemical changes under exercise conditions in pelvic floor musculature in a subject, comprising the steps of: (a) applying the vaginal imaging device described above to a subject at rest to acquire magnetic resonance spectroscopic data; (b) applying said vaginal imaging device to said subject during exercise to acquire magnetic resonance spectroscopic data; (c) applying said vaginal imaging device to said subject after exercise to acquire magnetic resonance spectroscopic data; and (d) comparing the data collected in (a), (b) and (c), wherein said comparison provides assessment of biochemical changes under exercise conditions in pelvic floor musculature in said subject.

The present invention is also directed to a method for assessing biochemical changes under exercise conditions in pelvic floor musculature in a subject, comprising the steps of: (a) applying the vaginal imaging device described above to a subject at rest to acquire magnetic resonance spectroscopic data; (b) applying said vaginal imaging device to said subject during exercise to acquire magnetic resonance spectroscopic data; (c) applying said vaginal imaging device to said subject after exercise to acquire magnetic resonance spectroscopic data; and (d) comparing the data collected in (a), (b) and (c), wherein said comparison provides assessment of biochemical changes under exercise conditions in pelvic floor musculature in said subject.

The present invention is also directed to a method for evaluating efficacy of a surgical repair in pelvic floor musculature in an individual, comprising the steps of: applying the vaginal imaging device described above to an individual before the surgical repair to produce a pre-surgery image of the pelvic floor musculature; applying said vaginal imaging device to said individual after the surgical repair to produce a post-surgery image of the pelvic floor musculature; and comparing said post-surgery image with said pre-surgery image, wherein differences in said images are indicative of the efficacy of said surgical repair.

The present invention is also directed to a method for evaluating efficacy of a surgical repair in pelvic floor musculature in an individual, comprising the steps of: applying the vaginal imaging device described above to an individual before the surgical repair to produce a pre-surgery image of the pelvic floor musculature and muscle function; applying said vaginal imaging device to said individual after the surgical repair to produce a post-surgery image of the pelvic floor musculature and muscle function; and comparing said post-surgery image with said pre-surgery image, wherein differences in said images are indicative of the efficacy of said surgical repair.

The present invention is also directed to a method for evaluating efficacy of an exercise therapy in an individual, comprising the steps of: applying the vaginal imaging device described above to an individual before said exercise therapy to produce a pre-therapy image of the pelvic floor musculature and muscle function; applying said vaginal imaging device to said individual after said exercise therapy to produce a post-therapy image of the pelvic floor musculature and muscle function; and comparing said post-therapy image with said pre-therapy image, wherein differences in said images are indicative of the efficacy of said exercise therapy.

The present invention is also directed to a method for evaluating efficacy of an exercise therapy in an individual, comprising the steps of: applying the vaginal imaging device described above to an individual before said exercise therapy to produce a pre-therapy image of the pelvic floor musculature and muscle function; applying the vaginal imaging device described above to said individual in the course of exercise therapy to produce an on-going assessment of the pelvic floor musculature and muscle function; applying said vaginal imaging device to said individual after said exercise therapy to produce a post-therapy image of the pelvic floor musculature and muscle function; and comparing said post-therapy image with said pre-therapy image, wherein differences in said images are indicative of the efficacy of said exercise therapy.

The present invention is also directed to a method for evaluating efficacy of a pharmaceutical therapy in an individual suffering from abnormalities in pelvic floor musculature, comprising the steps of: applying the vaginal imaging device described above to an individual before said pharmaceutical therapy to produce pre-therapy magnetic resonance spectroscopic data; applying said vaginal imaging device to said individual after said pharmaceutical therapy to produce a post-therapy magnetic resonance spectroscopic data; and comparing said post-therapy data with said pre-therapy data, wherein differences in said images are indicative of the efficacy of said pharmaceutical therapy.

The present invention is also directed to a method for evaluating efficacy of a pharmaceutical therapy in an individual suffering from abnormalities in pelvic floor musculature, comprising the steps of: applying the vaginal imaging device described above to said individual before said pharmaceutical therapy to produce pre-therapy magnetic resonance spectroscopic data; applying said vaginal imaging device to said individual after said pharmaceutical therapy to produce a post-therapy magnetic resonance spectroscopic data; and comparing said post-therapy data with said pre-therapy data, wherein differences in said images are indicative of the efficacy of said pharmaceutical therapy. The device of the present invention may also be device is suitable for rectal use in cases of fecal incontinence.

The following references were cited herein.

Astrand, P & Rodahl, K (1986) Textbook of work physiology: Physiological bases of exercise. New York: McGraw-Hill Book Company.

Bartolozzi, C et al., (1996). Eur. Radiol., 6(3): 339–345.

Bates, T S et al., (1996). Clin. Radiol., 51(8): 550–553.

Bo, K et al (1990). Neurourology and Urodynamics, 9, 489–502.

Boska, M (1991). NMR in Biomed., 4: 173–181.

Boska, M. (1994). Magn. Reson. Med., 32: 1–10.

Burns, P A et al. (1993). Journal of Gerontology: Medical Sciences, 48(4), M167–M174.

Christensen, L L et al. (1995). Neurourol Urodyn, 14(3), 209–216.

Critchley, H O D et al. (1980). Urologia Internationalis, 35, 226–232.

Dougherty, M et al. (1993). Journal of Reproductive Medicine, 38(9), 684–691.

Gilpin, S A et al. (1989). British Journal of Obstetrics and Gynecology, 96, 15–23.

Gufler, H et al. (1999). J. Magn. Reson. Imaging, 9(3), 378–83.

Hortobagyi, T et al. (1991). The Journal of Sports Medicine and Physical Fitness, 31(1), 20–30.

Huch Boni, R A et al. (1995). J. Compu. Assist. Tomogr., 19(2) 232–237.

Johnson V Y (2001). Effects of a submaximal exercise protocol to recondition the pelvic floor muscles, 50(1), 33–41.

Jones, E G & Kegel, A H (1952). Surgery, Gynecology, and Obstetrics, 94, 179–188.

Kegel, A H (1948) American Journal of Obstetrics and Gynecology, 56, 238–248.

Kegel, A H (1951) Journal of the American Medical Assoc., 146, 915.

Kegel, A H (1956) Journal International College of Surgeons, 25, 487.

Kegel, A H & Powell, T O (1950). Journal of Urology, 63, 808–814.
Kurhanewicz, J et al. (1991). Magn. Reson. Med., 22(2): 404–413.
Larson, et al. (1997) "Proc., ISMR, 5$^{th}$ Annual Mtg, 1997" p. 1302.
Newcomer, B et al. (1997). Muscle and Nerve, 20: 336–346.
Parks, A G et al. (1977). Gut, 18, 656–665.
Vanbeckevoort, D (1999). J. Magn. Reson. Imaging, 9(3), 373–377.
Wells, T (1990) Journal of the American Geriatric Society, 38(3), 333–337.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A vaginal imaging device, comprising:
    a single or dual tuned resonator comprising a transmit/receive element for nuclear magnetic resonance imaging and spectroscopy; and
    a force transduction mechanism for monitoring a subject's contraction effort and to permit triggering of a scanner to produce vaginal imaging and spectroscopy data.
2. The vaginal imaging device of claim 1, wherein said single tuned resonator is used for nuclear magnetic resonance imaging using the $^1$H isotope.
3. The vaginal imaging device of claim 1, wherein said dual tuned resonator is used for $^1$H isotope imaging and for performing nuclear magnetic resonance spectroscopy of a second isotope selected from the group consisting of $^{31}$P, $^{13}$C, $^{23}$Na, $^{39}$K and $^{43}$Ca.
4. The vaginal imaging device of claim 1, wherein said transmit/receive element is a single turn solenoid oriented to permit non-gradient localized spectroscopy.
5. The vaginal imaging device of claim 4, wherein a vial containing a 300 mM inorganic phosphate reference solution is located at the center of the loop of said single turn solenoid to allow chemical shift referencing for the signals obtained.
6. The vaginal imaging device of claim 1, wherein said transmit/receive element is an array of individual antenna elements located around the long axis of the device for the purpose of providing a different spatial sensitivity profile than that provided by a single turn solenoid.
7. The vaginal imaging device of claim 1, wherein said force transduction mechanism is used to monitor contraction effort of the subject for the purpose of synchronizing scanner image or spectroscopy data acquisition with the contraction effort of the subject.
8. The vaginal imaging device of claim 7, wherein said force transduction mechanism is used to synchronize scanner image acqustion with the scanner body volume resonator acting as the transmit/and or receive antenna.
9. The vaginal imaging device of claim 7, wherein said force transduction mechanism is used to synchronize scanner image or spectroscopy data acquisition with its own antenna element in a transmit/receive mode.
10. The vaginal imaging device of claim 7, wherein said force transduction mechanism is used to synchronize scanner image or spectroscopy data acquisition with its own antenna element in a receive only mode with active or passive decoupling, wherein said decoupling prevents local retransmit of the radiofrequency signal and excessive tissue heating.
11. The vaginal imaging device of claim 1, wherein said force transduction mechanism is selected from the group consisting of piezoelectric force transducer, resistive force transducer and pneumatic pressure transducer.
12. The vaginal imaging device of claim 1, wherein said imaging is selected from the group consisting of radiofrequency tagged magnetic resonance imaging, phase velocity mapping and diffusion weighted imaging.
13. The vaginal imaging device of claim 1, wherein said spectroscopy is non-gradient localized phosphorus spectroscopy.
14. A vaginal imaging device, comprising:
    (a) a single or dual tuned imaging and spectroscopy resonator and matching network;
    (b) a force transducer that produces a force proportional gating signal to trigger a scanner to produce vaginal imaging and spectroscopy data at user-defined force levels;
    (c) a magnetic resonance imaging compatible housing encasing (a) and (b);
    (d) a compliant and hollow disposable housing that allows pneumatic transduction of contraction effort, wherein said disposable housing contains the antenna element of said resonator; and
    (e) a mean to transmit the air pressure in said disposable housing to said force transducer located in the permanent housing.
15. The vaginal imaging device of claim 14, wherein said disposable housing may contain a locator ring to ensure correct positioning of said device.
16. The vaginal imaging device of claim 14, wherein an inflatable annular cuff that can be independently pressurized to provide for mechanical stabilization is located on the outside of said disposable housing near the tip.
17. The vaginal imaging device of claim 14, wherein said force transducer is selected from the group consisting of piezoelectric force transducer, resistive force transducer and pneumatic pressure transducer.
18. The vaginal imaging device of claim 14, wherein the antenna element of said resonator is a single turn solenoid oriented to permit non-gradient localized spectroscopy.
19. The vaginal imaging device of claim 18, wherein a vial containing a 300 mM inorganic phosphate reference solution is located at the center of the loop of said single turn solenoid to allow chemical shift referencing for the signals obtained.
20. The vaginal imaging device of claim 14, wherein said imaging is radiofrequency tagged magnetic resonance imaging.
21. The vaginal imaging device of claim 14, wherein said spectroscopy is non-gradient localized phosphorus spectroscopy.
22. The vaginal imaging device of claim 14, wherein said device is suitable for rectal use in cases of fecal incontinence.
23. A method for imaging pelvic floor musculature in a subject, comprising the step of:
    applying the vaginal imaging device of claim 1 to said subject to produce an image of the pelvic floor musculature.
24. A method for imaging pelvic floor musculature in a subject, comprising the step of:

applying the vaginal imaging device of claim 14 to said subject to produce an image of the pelvic floor musculature.

25. A method for obtaining spectroscopic information on the biochemical state of pelvic floor musculature in a subject, comprising the step of:
    applying the vaginal imaging device of claim 1 to said subject to produce magnetic resonance spectroscopic information which provides assessment of muscular biochemical activity.

26. A method for obtaining spectroscopic information on the biochemical state of pelvic floor musculature in a subject, comprising the step of:
    applying the vaginal imaging device of claim 14 to said subject to produce magnetic resonance spectroscopic information which provides assessment of muscular biochemical activity.

27. A method for assessing biochemical changes under exercise conditions in pelvic floor musculature in a subject, comprising the steps of:
    (a) applying the vaginal imaging device of claim 1 to said subject at rest to acquire magnetic resonance spectroscopic data;
    (b) applying said vaginal imaging device to said subject during exercise to acquire magnetic resonance spectroscopic data;
    (c) applying said vaginal imaging device to said subject after exercise to acquire magnetic resonance spectroscopic data; and
    (d) comparing the data collected in (a), (b) and (c), wherein said comparison provides assessment of biochemical changes under exercise conditions in pelvic floor musculature in said subject.

28. A method for assessing biochemical changes under exercise conditions in pelvic floor musculature in a subject, comprising the steps of:
    (a) applying the vaginal imaging device of claim 14 to said subject at rest to acquire magnetic resonance spectroscopic data;
    (b) applying said vaginal imaging device to said subject during exercise to acquire magnetic resonance spectroscopic data;
    (c) applying said vaginal imaging device to said subject after exercise to acquire magnetic resonance spectroscopic data; and
    (d) comparing the data collected in (a), (b) and (c), wherein said comparison provides assessment of biochemical changes under exercise conditions in pelvic floor musculature in said subject.

29. A method for evaluating efficacy of a surgical repair in pelvic floor musculature in an individual, comprising the steps of:
    applying the vaginal imaging device of claim 1 to said individual before the surgical repair to produce a pre-surgery image of the pelvic floor musculature;
    applying said vaginal imaging device to said individual after the surgical repair to produce a post-surgery image of the pelvic floor musculature; and
    comparing said post-surgery image with said pre-surgery image, wherein differences in said images are indicative of the efficacy of said surgical repair.

30. A method for evaluating efficacy of a surgical repair in pelvic floor musculature in an individual, comprising the steps of:
    applying the vaginal imaging device of claim 14 to said individual before the surgical repair to produce a pre-surgery image of the pelvic floor musculature and muscle function;
    applying said vaginal imaging device to said individual after the surgical repair to produce a post-surgery image of the pelvic floor musculature and muscle function; and
    comparing said post-surgery image with said pre-surgery image, wherein differences in said images are indicative of the efficacy of said surgical repair.

31. A method for evaluating efficacy of an exercise therapy in an individual, comprising the steps of:
    applying the vaginal imaging device of claim 1 to said individual before said exercise therapy to produce a pre-therapy image of the pelvic floor musculature and muscle function;
    applying said vaginal imaging device to said individual after said exercise therapy to produce a post-therapy image of the pelvic floor musculature and muscle function; and
    comparing said post-therapy image with said pre-therapy image, wherein differences in said images are indicative of the efficacy of said exercise therapy.

32. A method for evaluating efficacy of an exercise therapy in an individual, comprising the steps of:
    applying the vaginal imaging device of claim 14 to said individual before said exercise therapy to produce a pre-therapy image of the pelvic floor musculature and muscle function;
    applying the vaginal imaging device of claim 14 to said individual in the course of exercise therapy to produce an on-going assessment of the pelvic floor musculature and muscle function;
    applying said vaginal imaging device to said individual after said exercise therapy to produce a post-therapy image of the pelvic floor musculature and muscle function; and
    comparing said post-therapy image with said pre-therapy image, wherein differences in said images are indicative of the efficacy of said exercise therapy.

33. A method for evaluating efficacy of a pharmaceutical therapy in an individual suffering from abnormalities in pelvic floor musculature, comprising the steps of:
    applying the vaginal imaging device of claim 1 to said individual before said pharmaceutical therapy to produce pre-therapy magnetic resonance spectroscopic data;
    applying said vaginal imaging device to said individual after said pharmaceutical therapy to produce a post-therapy magnetic resonance spectroscopic data; and
    comparing said post-therapy data with said pre-therapy data, wherein differences in said images are indicative of the efficacy of said pharmaceutical therapy.

34. A method for evaluating efficacy of a pharmaceutical therapy in an individual suffering from abnormalities in pelvic floor musculature, comprising the steps of:
    applying the vaginal imaging device of claim 14 to said individual before said pharmaceutical therapy to produce pre-therapy magnetic resonance spectroscopic data;
    applying said vaginal imaging device to said individual after said pharmaceutical therapy to produce a post-therapy magnetic resonance spectroscopic data; and
    comparing said post-therapy data with said pre-therapy data, wherein differences in said images are indicative of the efficacy of said pharmaceutical therapy.

* * * * *